(12) United States Patent
Knox

(10) Patent No.: US 8,483,863 B1
(45) Date of Patent: Jul. 9, 2013

(54) SURGICAL BONE AND CARTILAGE SHAPING ON DEMAND WITH 3D CAD/CAM

(76) Inventor: Glenn Knox, Jacksonville, FL (US)

( * ) Notice: Subject to any disclaimer, the term of this patent is extended or adjusted under 35 U.S.C. 154(b) by 505 days.

(21) Appl. No.: 12/711,839

(22) Filed: Feb. 24, 2010

Related U.S. Application Data

(60) Provisional application No. 61/215,994, filed on May 12, 2009.

(51) Int. Cl.
*G06F 19/00* (2011.01)

(52) U.S. Cl.
USPC .............. 700/118; 700/98; 700/119; 700/182

(58) Field of Classification Search
None
See application file for complete search history.

(56) References Cited

U.S. PATENT DOCUMENTS

| | | | | |
|---|---|---|---|---|
| 4,192,021 A * | 3/1980 | Deibig et al. | ............... | 623/23.61 |
| 4,663,720 A * | 5/1987 | Duret et al. | ................... | 700/163 |
| 4,742,464 A * | 5/1988 | Duret et al. | ................... | 700/183 |
| 4,936,862 A * | 6/1990 | Walker et al. | ................. | 128/898 |
| 5,150,304 A * | 9/1992 | Berchem et al. | ............. | 700/182 |
| 5,257,203 A * | 10/1993 | Riley et al. | ..................... | 700/163 |
| 5,274,565 A * | 12/1993 | Reuben | ......................... | 700/182 |
| 5,448,489 A * | 9/1995 | Reuben | ......................... | 700/163 |
| 5,452,407 A * | 9/1995 | Crook | ........................... | 345/421 |
| 5,880,964 A * | 3/1999 | Schall et al. | .................. | 700/159 |
| 6,572,572 B2 * | 6/2003 | Pomatto et al. | .................. | 602/17 |
| 6,733,747 B2 * | 5/2004 | Anderson et al. | .......... | 424/93.21 |
| 7,131,605 B2 * | 11/2006 | McPherson et al. | ..... | 241/199.12 |
| 7,147,846 B2 * | 12/2006 | Anderson et al. | .......... | 424/93.21 |
| 7,383,094 B2 * | 6/2008 | Kopelman et al. | ............. | 700/118 |
| 7,447,556 B2 * | 11/2008 | McBagonluri et al. | ......... | 700/98 |
| 7,483,558 B2 * | 1/2009 | Greene et al. | ................. | 382/131 |
| 7,747,305 B2 * | 6/2010 | Dean et al. | ..................... | 600/407 |
| 7,996,099 B2 * | 8/2011 | Kopelman et al. | .............. | 700/98 |
| 8,060,236 B2 * | 11/2011 | Hilliard | ......................... | 700/160 |
| 8,062,372 B2 * | 11/2011 | Tsuang et al. | .............. | 623/17.16 |
| 8,086,336 B2 * | 12/2011 | Christensen | .................... | 700/98 |
| 8,160,345 B2 * | 4/2012 | Pavlovskaia et al. | ......... | 382/131 |
| 8,200,355 B2 * | 6/2012 | Lee et al. | ....................... | 700/118 |
| 8,221,430 B2 * | 7/2012 | Park et al. | ........................ | 606/88 |
| 2005/0261795 A1 * | 11/2005 | Ghosh et al. | .................. | 700/118 |
| 2007/0264612 A1 * | 11/2007 | Mount | .......................... | 433/173 |
| 2007/0276501 A1 * | 11/2007 | Betz et al. | .................. | 623/17.16 |
| 2009/0081076 A1 * | 3/2009 | Baege et al. | ..................... | 422/28 |
| 2009/0287332 A1 * | 11/2009 | Adusumilli et al. | ............. | 700/98 |
| 2009/0292379 A1 * | 11/2009 | Pitz | .................................. | 700/98 |
| 2010/0114351 A1 * | 5/2010 | Kopelman et al. | .............. | 700/98 |
| 2010/0152873 A1 * | 6/2010 | Dunne et al. | .................... | 700/98 |
| 2010/0268363 A1 * | 10/2010 | Karim et al. | ..................... | 700/98 |
| 2011/0106093 A1 * | 5/2011 | Romano et al. | ................. | 606/88 |

* cited by examiner

*Primary Examiner* — Kavita Padmanabhan
*Assistant Examiner* — Christopher E Everett
(74) *Attorney, Agent, or Firm* — Lawrence J. Gibney, Jr.

(57) ABSTRACT

In order to effectuate proper construction of prosthetic devices during surgery, a device that will shape the prosthetic device from the patient's own tissue has been contemplated. Although ear surgery requires exacting measurements because of the size that is involved is discussed, many other types of artificial devices can be manufactured during a number of different types of procedures to include orthopedic and dental prosthesis. Many different types of tissues may be used and a computer with associated software will enable a milling machine to manufacture the required prosthetic device at the time of the procedure.

10 Claims, 1 Drawing Sheet

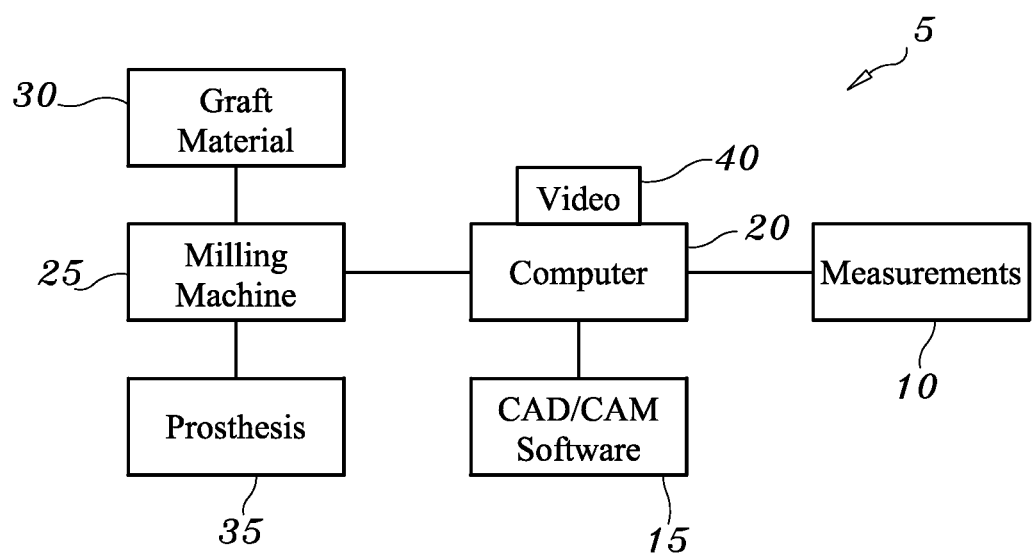

SURGICAL BONE AND CARTILAGE SHAPING ON DEMAND WITH 3D CAD/CAM

CROSS-REFERENCE TO RELATED APPLICATIONS

This is a continuation of a prior provisional application that was filed on May 12, 2009 with an application number of 61/215,994.

BACKGROUND OF THE INVENTION

A. Field of the Invention

This relates to making prosthetic devices during ear surgery as well as other otolaryngolical, orthopedic or dental prostheses. The great advantage of this application is that it is made onsite at the time of the surgery so that the surgeon performing ear surgery can immediately shape it to the patient for completion of the surgical procedure.

B. Prior Art

There are prior art references to prosthetic grafts. A representative example of this can be found at Anderson, U.S. Pat. No. 7,147,846. This particular application teaches a porous prosthetic implant suitable for repair of blood vessels, which also discloses the method for making and using such a graft.

Another example of this is found at Anderson, U.S. Pat. No. 6,733,747, and Anderson, U.S. Pat. No. 6,328,762. None of these prior art references use 3-D CAD or CAM software to produce the grafted material at the time of a surgery.

Another prior art reference is found at Mount, U.S. patent publication number 2007/0264612. This reference employs the used of CAD and CAM technology to manufacture an implant for eventual insertion into the person's mouth. It does not contemplate the manufacture at the time of the procedure as is taught in this application.

BRIEF SUMMARY OF THE INVENTION

This is a method for making a bone and cartilage graft from autologous, homologous, or xenologous tissues as the graft material. Although there may be additional applications such as otolarnygological orthopedic surgery, this will become particularly important in ear surgery that involves precise measurements in confined spaces.

During or prior to an ear surgery, measurements are taken to determine the size, shape, and configuration of the desired graft. Measurements may also be taken prior to surgery as well. These measurements are then entered into a computer with 3-D CAD/CAM software and the harvested graft material is inserted into a milling machine, which is akin to a 3-D CAD printer. After the prosthetic graft is milled, the graft is removed and surgically implanted. In addition, the milling machine 3-D printer has removable parts, which can then be autoclaved or gas sterilized for reuse.

This device will be particularly important in many autologic procedures, which typically involve minute, precisely shaped bone and cartilage grafts. These grafts are often used to construct or reconstruct the eardrum or sound-connecting mechanism of the middle ear. Smaller grafts are sometimes used to show off the open end of the posterior semicircular canal to control positional vertigo. Because of the minute clearances, the shaping of the graft intraoperatively is quite difficult given the fact they require microscopic dissection and fitting.

This invention will allow convenient, rapid intraoperative generation of suitable grafts during otologic microsurgery at the time of surgery.

BRIEF DESCRIPTION OF THE DRAWINGS

FIG. 1 is a schematic of the components of this device.

DETAILED DESCRIPTION OF THE EMBODIMENTS

During certain operative procedures it is important to be able to construct prosthetic devices at the time of the procedure in order to complete the surgery without requiring the patient to return for another appointment for installation of the prosthetic device.

Although this application will have many medical applications to manufacture grafts, prosthetic grafts as they relate to the ear will be discussed in this application.

Because of the minute structure of the ear and the exacting dimensions, ear prosthetic devices require exacting measurements in order to function effectively.

With regard to the procedures related to the ear, and because the ear prosthetics require exacting measurement, this invention will aid the practitioner during such procedures.

This is a method for making bone and/or cartilage grafts from autologous, homologous, or xenologous tissues. The principal advantage of making the graft from one of these types of tissues is that synthetic material can be extruded but become infected due to "foreign body reactions". The above referenced tissues do not carry the amount of risk of foreign body reactions as synthetic tissues. During the procedure it is preferable to use autologous tissues, which have the lowest rate of rejection, although all types of tissues can be used.

During or prior to the procedure measurements 10 are taken to determine the exact size of the graft that will need to be constructed. These measurements are necessary to determine the exact shape and size of the graft.

The measurements 10 are inputted into computer software 15. The graft material 30 is placed in a milling machine 25, which is operated by a computer 20 and its associated CAD/CAM software 15 and a suitable prosthetic 35 is made from the graft material 30. A video image 40 on the computer screen of the graft 30 is available.

The milling machine 25 has removable parts so that the parts can be sterilized between procedures.

A principal advantage to this invention is that the graft material 30 can form a new prosthetic at the time of surgery. Because of the minute clearances and exacting measurements that are required with an otologic prosthesis, the milling machine 25 will form the graft to exacting specification according to the measurements. The manufacture of the prosthetic device can occur during the time of surgery and the new prosthetic device is ready for use immediately after being milled.

While the embodiments of the invention have been disclosed, certain modifications may be made by those skilled in the art to modify the invention without departing from the spirit of the invention.

The invention claimed is:

1. A surgical bone and cartilage shaping device which is comprised of the following:
 a. a computer;
 wherein predetermined measurements are taken concerning a graft repair;
 said measurements concerning the graft repair are provided to the computer;
 wherein a video screen is provided on the computer;
 b. graft material;

wherein graft material is selected to form a prosthetic device;

said graft material is harvested from a patient during surgery on the patient;

wherein the graft material is placed in a milling machine during the surgery;

c. computer software;

wherein the computer software is integrated with the computer;

d. the milling machine;

wherein the milling machine forms the prosthesis;

wherein the milling machine forms the prosthesis by subtracting portions of the graft material as determined by the measurements required for the graft repair;

said milling machine is integrated with the computer and the computer software;

e. the prosthesis;

wherein the prosthesis is formed by the milling machine according to the measurements required for the graft repair;

said prosthesis is placed in the patient during the surgery.

2. A surgical bone and cartilage shaping device as described in claim 1 wherein the graft material is selected from autologous tissues.

3. A surgical bone and cartilage shaping device as described in claim 1 wherein the milling machine has removable parts.

4. A surgical bone and cartilage shaping device as described in claim 1 wherein the computer software is computer aided design (CAD) software.

5. A surgical bone and cartilage shaping device as described in claim 1 wherein the computer software is computer aided manufacturing (CAM) software.

6. A method for manufacturing a customized bone graft using the device as described in claim 1 wherein the computer is connected to the milling machine; wherein said milling machine is a specialized 3D CAD/CAM printer.

7. A method for manufacturing a customized bone graft using the device as described in claim 1 wherein the graft material is shaped in the milling machine and milled to the measurements required for the graft repair.

8. A method for manufacturing a customized bone graft using the device as described in claim 1 wherein a part of the milling machine can be cleaned by a sterilization method.

9. The method as described in claim 8 wherein the sterilization method is autoclaving.

10. The method as described in claim 8 wherein the sterilization method is gas sterilization.

* * * * *